United States Patent [19]

Brandon

[11] Patent Number: 4,980,166

[45] Date of Patent: Dec. 25, 1990

[54] METHOD OF REGULATING ANIMAL REPRODUCTION

[75] Inventor: Malcolm R. Brandon, Ivanhoe, Australia

[73] Assignee: Bunge (Australia) Pty. Ltd., Victoria, Australia

[21] Appl. No.: 44,305

[22] Filed: Apr. 30, 1987

[30] Foreign Application Priority Data

May 2, 1986 [AU] Australia .............................. PH 5717

[51] Int. Cl.$^5$ ............................................ A61K 37/24
[52] U.S. Cl. ..................................... 424/565; 514/12; 514/800; 514/21; 514/8; 422/61
[58] Field of Search ........................... 514/12, 15, 800; 422/61; 424/108

[56] References Cited

U.S. PATENT DOCUMENTS 4,128,638  12/1978  Moody .................................. 514/15
4,599,227   7/1986  Dees ..................................... 514/12

OTHER PUBLICATIONS

W. M. C. Maxwell and H. R. Wilson, "Superovulation and Embryo Recovery in Ewes Treated with a Single Injection of PMSG and FSH-P," Australian Society for Reproductive Biology, Proceedings of the Twenty First Annual Conference (Sep. 25-27, 1989), p. 50.

B. M. Bindon et al., "Ovulatory Response to Exogenous FSH by Cattle Selected for Twin Births," Australian Society for Reproductive Biology, Proceedings (dated 1986), p. 44.

Y. Cognie and S. Torres, "Ovarian Response, Ova Recovery and Fertilization Rate After Superovulation With FGA and pFSH in the Ewe," 10th International Congress on Animal Reproduction and Artificial Insemination, University of Illinois at Urbana-Champaign, Illinois, USDA (Jun. 10-14, 1984).

G. H. Larson et al., "Follicle Stimulating Hormone Pattern and Luteal Function in Ewes Receiving Bovine Follicular Fluid During Three Stages of the Estrous Cycle," *J. Animal Science*, 64, 1491-1497 (May 1987).

*Primary Examiner*—F. T. Moezie
*Attorney, Agent, or Firm*—Merchant, Gould, Smith, Edell, Welter & Schmidt

[57] ABSTRACT

A method of inducing or increasing ovulation in female animals which method includes administering to the animal an effective amount of a ruminant follicle-stimulating hormone, (as hereinbefore defined).

20 Claims, No Drawings

METHOD OF REGULATING ANIMAL REPRODUCTION

This invention relates to a method of regulating the reproductive functions of animals, in particular female animals, and to veterinary compositions for use in such a method.

It is known in the prior art to regulate reproductive functions in female animals in a variety of ways. Artificial and natural products such as prostaglandins, pregnant mare serum gonadotrophin, melatonins and the like have been proposed for regulation of reproduction in animals. However, such treatments have proved of limited value in inducing or increasing ovulation in female animals.

One treatment known in the prior art includes the treatment of animals with a product incorporating porcine follicle-stimulating hormone (P-FSH). While such treatments have proved to be effective, it has been found necessary to utilise relatively high dosage rates which are therefore expensive and may lead to complications, due to over-stimulation, including ovarian damage, generalised oedema, and adhesions and may impair subsequent fertility. Moreover, difficulties have been found in the quality of embryos subsequently produced and a high proportion of unviable embryos has been found to be common.

It is therefore an object of the present invention to overcome, or at least alleviate, one or more of the difficulties related to the prior art.

Accordingly, in accordance with a first aspect of the present invention there is provided a method of inducing or increasing ovulation in female animals which method includes administering to the animal an effective amount of a ruminant follicle-stimulating hormone, (as hereinbefore defined).

By the term "follicle-stimulating hormone" as used herein in the description and claims we mean a natural or synthetic follicle-stimulating hormone, a derivative thereof or bioprecursor therefor.

By the term "bioprecursor" as used herein in the description and claims we mean any compound which exhibits follicle-stimulating hormone-like activity in animals.

The follicle-stimulating hormone may be an ovine, caprine or bovine follicle-stimulating hormone. A follicle-stimulating hormone isolated from a sexually immature animal is preferred. The animals to be treated may be selected from sheep, goats, cattle, deer, dogs, cats, pigs and the like.

The method of treating the female animal may be of any suitable type. The treatment may be oral, by injection, by implant or the like. Accordingly, the follicle stimulating hormone may be provided in a unit dosage form. An oral form, an injectable form or an implant form may be used. The follicle-stimulating hormone may be in a lyophilised form.

The follicle-stimulating hormone may be provided from natural or synthetic sources including the cloning of the gene coding for a follicle-stimulating hormone which is a polypeptide and its expression in prokaryotic and eukaryotic organisms, or a product thereof may also be used. The follicle-stimulating hormone may be extracted from the pituitary gland of ruminant animals. The pituitary glands of sheep may be used. The pituitary glands of lambs are preferred. The pituitary glands of cattle may be used. The pituitary glands of calves are preferred. The pituitary glands of goats may be used. The pituitary glands of kids are preferred. Ovine follicle stimulating hormone isolated from the pituitary glands of lambs has been found to be surprisingly more effective than other forms.

It has been surprisingly found that a ruminant follicle-stimulating hormone provides an improved yield of ova relative to other treatments including treatment with P-FSH. An increased yield of approximately 50% or greater may be provided. Moreover, it has been found that embryos produced from ova induced by a ruminant follicle-stimulating hormone are of improved quality relative to prior art treatments and damage to the ovaries of the treated animals is surprisingly reduced. The embryos so produced are characterised by an increased viability.

The amount of the ruminant follicle-stimulating hormone to be used will vary with the species of animal to be treated and the reproductive function to be achieved. Accordingly, in a preferred form the present invention provides a method of increasing the number of ova produced during ovulation in female animals, which method includes administering to the animal an effective amount of a ruminant follicle-stimulating hormone, a derivative thereof or bioprecursor therefor for a period sufficient to induce increased ova production.

The individual dose rates may vary from approximately 4 mg to approximately 30 mg. The treatment may comprise a single dose. The treatment may continue for from approximately 1 to 10 days. The selection of dose rates is dependent on the size age and species of animal to be treated. It has been found suitable to reduce the dosage rate over the treatment period. A dosage rate of approximately 3 to 10 mg per day reducing to approximately 0.4 to 2 mg per day over a period of 1 to 4 days has been found to be a suitable dosage regimen for sheep. An increased dosage regimen may be utilised for cattle.

The selection of dose rates is also dependent on the source of follicle stimulating hormone. The range of dose rates stated above relates to FSH isolated from natural sources including isolation from harvested pituitary glands of animals. Such "natural" FSH may include a high level of impurities. FSH having a higher purity for example where formed via a synthetic route may be administered at substantially reduced dose rates.

For example dose rates of from approximately 80 ug to approximately 600 ug may be used.

In a preferred form of this aspect of the present invention there is provided a method of increasing ovulation to provide twinning in female cattle, which method includes treating a cow with an amount of approximately 1 to 20 mg of a ruminant follicle-stimulating hormone.

The treatment may comprise a single dose. The dosage rate may be given in reducing amounts. The treatment may continue over a period of approximately 1 to 4 days.

In a preferred form the dosage regimen includes administration of approximately 1 to 10 mg per day of ovine follicle stimulating hormone in 1 to 5 doses over a period of one day. It has been surprisingly found that twinning may be induced in cattle on a relatively consistent basis utilising a ruminant follicle-stimulating hormone in cattle preferably ovine FSH. It will be understood that twinning is ideal in cattle production. The production of a single calf is an inefficient use of resources, whereas the production of 3 or more ova and thus embryos may often result in deformities and/or spontaneous abortion in cattle. Preferably, the cattle treated are sexually mature.

In an alternative form of this aspect of the present invention there is provided a method of inducing ovulation in pre-pubescent female animals which method includes administering to an animal an effective amount of a ruminant follicle-stimulating hormone for a period sufficient to induce ovulation. The ruminant follicle-stimulating hormone may be ovine FSH.

The amount of ovine follicle-stimulating hormone used may vary from approximately 1 to 20 mg, preferably 7 to 9 mg. The pre-pubescent animals may be treated with a single dose. The pre-pubescent animals may be treated at reducing dosage rates over a period of approximately 1 to 5 days.

In a preferred form, the method of inducing or increasing ovulation to produce twinning or otherwise, may include the preliminary step of treating the animal with an effective amount of a synchronising agent. The synchronising agent may be selected from any of the agents known per se. The agent may be a progestagen, prostaglandin, prostaglandin analogue or the like. Synchronising agents sold under the trade designation Chronogest (available Intervet (Australia) and "Repromap" (available from Upjohn Pty. Ltd.) intravaginal sponges have been found to be suitable in sheep and goats. The synchronising agent sold under the trade designation Estrumate (available from ICI Australia Ltd.) has been found to be suitable for cattle.

The preliminary treatment with the synchronising agent or the like may be undertaken at a preselected interval of time prior to the initiation of treatment with the ruminant follicle-stimulating hormone. The treatment with synchronising agent may be undertaken approximately 8 to 15 days prior to FSH treatment.

It has been found that the synchronising treatment in combination with the ovine FSH treatment was effective in inducing ovulation in pre-pubescent female cattle of approximately 10 months of age.

Preferably approximately 250 ug to approximately 100 mg of a synchronising agent is administered to a pre-pubescent animal approximately 8 to 15 days prior to initiation of ovine follicle-stimulating hormone treatment. The treatment with synchronising agent may be repeated at a suitable interval if necessary.

Preferably approximately 500 ug to 1000 ug of synchronising agent is used in the treatment of cattle via an injectable synchronising agent such as "Estrumate".

Preferably approximately 25 to 75 mg of synchronising agent is used in the treatment of sheep and goats via a synchronising agent of the intravaginal-sponge type such as Repromap or Chronogest.

In a more preferred form, the method of inducing or increasing ovulation to produce twinning or otherwise may include the further step of treating the animal with an effective amount of a luteinizing agent during or after the ovine FSH treatment. The luteinizing agent may be a prostaglandin or prostaglandin analogue. The luteinizing agent may be the same as, or different to the synchronising agent previously described.

Preferably the luteinizing agent is a prostaglandin or prostaglandin analogue and is administered in an amount of approximately 250 ug to approximately 1000 ug approximately 1 to 3 days after the initiation of ruminant follicle-stimulating hormone treatment.

In a further preferred form the method of inducing or increasing ovulation may include the further step of administering to the animal an effective amount of gonadotrophin or derivative thereof.

It has been found that some animals in some trials of the order of 20% do not respond to the ruminant FSH treatment done. It has now been found that an additional treatment with a relatively small amount of a gonadotrophin or derivative thereof results in a substantial reduction of the number of animals who are not responding.

A pregnant mare serum gonadotrophin (PMSG) may be used. A pregnant mare serum gonadotrophin of the type described in Australian provisional patent application PH 8482/86 has been found to be suitable (the entire disclosure of which is incorporated herein by reference). More preferably the monoclonal antibody derived therefrom disclosed therein may be used. PMSG is also referred to as equine chorionic gonadotrophin (eCG).

The gonadotrophin or derivative thereof may be administered in amounts of from approximately 100 i.u to 1000 i.u. and preferably 500 i.u.

The gonadotrophin treatment may be administered at any time during or before the ovine FSH treatment. Preferably the gonadotrophin treatment may be undertaken on the first day of the ovine FSH treatment.

In a further aspect of the present invention there is provided a veterinary composition including an effective amount of a ruminant follicle-stimulating hormone. The ruminant follicle-stimulating hormone may be an ovine follicle-stimulating hormone.

The ovine follicle-stimulating hormone or derivative may be provided in a lyophilised form. The veterinary composition may further include a veterinarily acceptable carrier or excipient. The carrier or excipient may be a solvent for the follicle stimulating hormone or derivative. An aqueous solvent may be used. A physiologically acceptable saline buffered solvent may be used. The veterinary composition may be provided in an injectable form.

In a preferred form of this aspect of the present invention there is provided the veterinary composition further includes an effective amount of a gonadotrophin or gonadotrophin analogue.

In a preferred form the present invention provides a kit of Parts including a supply of ovine follicle-stimulating hormone in a lyophilised form in a suitable container.

The kit of parts may further include a supply of a synchronising agent in a suitable container. The ovine follicle-stimulating hormone, gonadotrophin, and the synchronising agent where present, may be provided in an injectable form.

The present invention will now be more fully be understood, however, that the description following is illustrative only and should not be taken in any way as a restriction on the generality of the invention described above.

EXAMPLE 1

The ovine follicle-stimulating hormone (O-FSH) was prepared in the following way:

Frozen whole lamb pituitaries were ground and extracted overnight with distilled water, pH 5.5. The resulting FSH-rich extract was fractionated successively with 1.80M ammonium sulphate, pH 4.0 to remove inert proteins, and the FSH precipitated with 3.0 M ammonium sulphate, pH 4.0. The FSH preparation was neutralised with NaOH, dialysed against distilled water, and lyophilized. All steps of this procedure were carried out in a cold room at 5° C.

EXAMPLE 2

Field trials were conducted on sheep utilising ovine follicle-stimulating hormone (O-FSH). The sheep were treated utilising the following treatment regimen:

Sheep Regimen for FSH 8 injections over 4 days (a.m.,p.m.) in decreasing amounts in the ratio of 4:3:2:1 For example

| 8 mg as follows: | Day 1 - a.m. | 1.6 |
| | - p.m. | 1.6 |
| | Day 2 - a.m. | 1.2 |
| | - p.m. | 1.2 |
| | Day 3 - a.m. | 0.8 |
| | - p.m. | 0.8 |
| | Day 4 - a.m. | 0.4 |
| | - p.m. | 0.4 |
| Treatment Schedule | | |
| Day 1 - REPROMAP* sponge inserted | | |
| Day 10 - day 1 of injection of FSH a.m./p.m. | | |
| Day 11 - day 2 FSH a.m./p.m. | | |
| Day 12 - sponge withdrawal day 3 FSH a.m./p.m. | | |
| Day 13 - day 4 FSH a.m./p.m. | | |

*Intravaginal sponge (60 mg of Medroxyprogesterone acetate)

The results of three field trials including a comparison with ewes treated with the commercially available P-FSH (available from ESSEX/Heriot, Melbourne) are set out in Tables 1, 2 and 3.

TABLE 1

| | Trial 1 Random Bred Merinos | | | | |
|---|---|---|---|---|---|
| | Dose Total mg | Ewes treated | Ovulated following treatment | Ovulation Rate* Mean | Range |
| Ovine FSH | 8 | 8 | 7 | 4.25 | 1-19 |
| | 4 | 7 | 7 | 1.6 | 1-3 |
| | 2 | 8 | 6 | 1.2 | 1-2 |
| Commercial Product P-FSH | 8 | 7 | 7 | 2.4 | 1-5 |
| | 4 | 6 | 5 | 1.2 | 1-2 |

*of those ovulating

TABLE 2

| | Trial 2 Random Bred Merinos | | | | |
|---|---|---|---|---|---|
| | Dose Total mg | Ewes Treated | Ovulated following treatment | Ovulation Rate Mean | Range |
| Ovine FSH | 8 | 8 | 6 | 5.83 | 1-14 |
| | 4 | 9 | 9 | 1.33 | 1-2 |
| | 2 | 9 | 9 | 1.67 | 1-3 |
| | 0 | 8 | 8 | 1.25 | 1-2 |
| P-FSH | 8 | 8 | 7 | 3.71 | 1-11 |
| | 4 | 8 | 8 | 1.38 | 1-2 |
| | 0 | 8 | 8 | 1.25 | 1-2 |

*of those ovulating

TABLE 3

| | Trial 3 First Cross Ewes (Border Leicester × Merino) | | | | |
|---|---|---|---|---|---|
| | Dose Total mg | Ewes Treated | Ovulated following treatment | Ovulation Rate* Mean | Range |
| Ovine FSH | 12+ | 12 | 11 | 10.2 | 2-23 |
| P-FSH | 18+ | 6 | 6 | 4.3 | 1-6 |

*of those ovulating
+In this field trial the FSH was administered AM, PM over 3 days starting at Day 10 after sponge insertion.

The amounts (mg) of O-FSH injected were 3,3,2,2,1,1 of P-FSH injected were 4,4,3,3,2,2

EXAMPLE 3

Excellent results were obtained with O-FSH in sheep in contrast to P-FSH. However up to 20% of sheep failed to ovulate using O-FSH or P-FSH. This problem was solved by using a small amount of PMSG in conjunction with FSH treatment, resulting in up to 100% of sheep ovulating. The PMSG was preferably that described in Australian provisional patent application No. PH 8482/86 or less preferably the commercially available product Folligon (Intervet, Melbourne). The O-FSH proved to be far superior to that of P-FSH when used in conjunction with PMSG.

Field trials were conducted on sheep utilising ovine follicle stimulating hormone (O-FSH) and PMSG.

The sheep were treated utilising the following treatment regimen:

Sheep Regimen for O-FSH

Injections over 3 days (a.m., p.m.) in decreasing amounts in the ratio of 3:2:1

| 12 mg as follows: | Day 1 - a.m. | 3 |
| | - p.m. | 3 |
| | Day 2 - a.m. | 2 |
| | - p.m. | 2 |
| | Day 3 - a.m. | 1 |
| | - p.m. | 1 |
| Treatment Schedule | | |
| Day 1 - Chronogest* sponge inserted (30 mg.) | | |
| Day 10 - 500 i. u. PMSG day 1 of injection FSH am/pm | | |
| Day 11 - day 2 of injection FSH am/pm | | |
| Day 12 - sponge withdrawl day 3 FSH am/pm | | |
| Day 13 - Endoscopic artificial insemination PM | | |
| Day 19/20 - Flushing of embryos | | |

*Intravaginal sponge (30 mg flugestone acetate)

TABLE 5

| | Trial 4 | | | | |
|---|---|---|---|---|---|
| | Dose (mg) Total | Ewes treated | Ovulated following treatment | Ovulation Rate* Mean | Range |
| 50 kg Merino Ewes | | | | | |
| Ovine FSH 500 i. u. PMSG | 12 | 16 | 16 | 15.1 | 2-32 |
| 50 kg Merino Ewes | | | | | |
| P-FSH 500 i. u. PMSG | 12 | 25 | 20 | 9.0 | 1-25 |
| 50 kg Comeback Ewes | | | | | |
| Ovine FSH | 12 | 11 | 11 | 13.6 | 6-19 |

TABLE 5-continued

| | Trial 4 | | | |
|---|---|---|---|---|
| Dose (mg) Total | Ewes treated | Ovulated following treatment | Ovulation Rate* Mean | Range |
| 500 i. u. PMSG | | | | |
| 60 kg Southdown Ewes | | | | |
| Ovine FSH 500 i. u. PMSG | 12 | 11 | 11 | 10.2 4–21 |

*of those ovulating

Observations on Trial 4

1. Fertilisation rate using fresh semen ≧95% with O-FSH.
2. In all cases where O-FSH was used the anatomy of the ovaries was unaltered, whereas where P-FSH was used ovaries were distorted and not normal in anatomical appearance.
3. Using P-FSH still 20% of ewes did not ovulate even though a small amount of PMSG used. With O-FSH 100% of sheep ovulated regardless of whether Merino or British-type breeds.
4. Of the Merino sheep treated 50% more embryos using O-FSH v P-FSH.
5. Different breeds give different responses. Using P-FSH especially in British-type breeds very poor responses were observed.

TABLE 6

| | Trial 5 | | | |
|---|---|---|---|---|
| Dose (mg) Total | Ewes Treated | Ovulated following treatment | Ovulation Rate* Mean | Range |
| 50 kg COMEBACK EWES | | | | |
| Ovine FSH 500 i.u. PMSG | 12 15+ | 10 8 | 10 8 | 13.6 6–19 15.0 5–23 |
| 60 kg SOUTHDOWN EWES | | | | |
| Ovine FSH 500 i.u. PMSG | 12 15 | 11 12 | 11 12 | 10.2 4–21 11.4 6–20 |

*of those ovulating
+The amounts of 0-FSH injected were 3, 3, 2.5, 2.5, 2, 2

Observations on Trial 5

1. Increasing the dose of O-FSH made slight improvement in the ovulation rates of both Merino type and English type sheep.
2. Anatomy of ovaries still fine

EXAMPLE 4

Field trials were conducted on goats utilising ovine follicle-stimulating hormone (O-FSH). The goats were treated utilising the following treatment regimen:

Goat Regimen for O-FSH

Injections over 3 days (am/pm) in decreasing amounts in the ratio of 3:2:1

| 12 mg as follows | Day 1 - am | 3 |
|---|---|---|
| | - pm | 3 |
| | Day 2 - am | 2 |
| | - pm | 2 |
| | Day 3 - am | 1 |
| | - pm | 1 |
| Treatment Schedule | | |

Day 1 - Chronogest Sponge inserted (40 mg)
Day 16 - Group 6a: no PMSG ⎫ day 1 of injection -continued Group 6b: 400 i.u. PMSG ⎭ FSH am/pm Day 17 - day 2 of injection FSH am/pm
Day 18 - Sponge withdrawal day 3 FSH am/pm
Day 20 - Endoscopic artificial insemination or natural mating
Day 26 - Flushing of embryos.

TABLE 7

| | Dose (mg) Total | Ewes Treated | Ovulated following treatment | Ovulation Rate* | |
|---|---|---|---|---|---|
| | | | | Mean | Range |
| | Trial 6a Feral Goats | | | | |
| Ovine FSH | 12 | 21 | 14 | 12.7 | 1–33 |
| Saline (Controls) | 0 | 18 | 14 | 2.0 | 1–3 |
| | Trial 6b Angora Goats | | | | |
| Ovine FSH 400 i.u. PMSG | 12 | 9 | 9 | 10.2 | 4–20 |

*of those ovulating

In goats of similar weight and age using 15 mg P-FSH and 400 i.u. PMSG other researchers have only obtained from 3 to 8 ovulations.

Observations on Trials 6a & 6b

1. Use of PMSG/O-FSH results in 100% ovulation rate for goats.
2. Anatomy of ovaries unchanged—a significant problem with P-FSH.
3. ≧95% fertilisation rate using fresh semen with O-FSH.

EXAMPLE 5

Field trials were conducted on cattle utilising ovine follicle-stimulating hormone (O-FSH). The cattle were treated with O-FSH in 8 injections over 4 days (am, pm) in decreasing amounts in the ratio of 4:3:2:1.

Treatment Schedule

The oestrous cycles were synchronised by two injections 500 ug, intramuscular of a prostaglandin analogue (Estrumate, ICI) at 11 day intervals. On day 8–10 of the subsequent cycle the animals commenced a 4 day FSH treatment (2 subcutaneous injections per day at 0900 and 1600 hr) with the total dose of FSH being given in a decreasing ratio of 4:3:2:1 over the 4 days. The prostaglandin analogue was again injected on the morning of the third day of FSH injection.

The ovulation rate was assessed by laproscopy under Barbiturate anaesthesia 4–6 days after oestrous or by non-surgical flushing of embryos.

TABLE 8

Trial 7
Field trial conducted on nulliparous Hereford Heifers aged 3 years with superovulation induced by O-FSH and P-FSH

|  | Dose Total (mg) | Cattle Treated | Ovulated Following Treatment | Ovulation Rate Mean | Range |
|---|---|---|---|---|---|
| Ovine FSH | 0 | 6 | 6 | 1.0 | 1-1 |
|  | 10 | 6 | 6 | 2.3 | 1-4 |
|  | 30 | 7 | 7 | 13.7 | 10-19 |
| P-FSH | 0 | 6 | 6 | 1.0 | 1-1 |
|  | 10 | 6 | 6 | 1.2 | 1-2 |
|  | 30 | 7 | 7 | 7.9 | 1-19 |

Observations on Trial 7

(1) Excellent superovulatory response to 30 mg O-FSH
(2) Very uniform ovulatory response with no ovarian over-stimulation using O-FSH. However with P-FSH both were a problem.

A field trial was conducted to illustrate the method of inducing ovulation in pre-pubescent animals according to the present invention.

Treatment Protocol (a) 2×Estrumate injections 11 days apart
(b) Begin O-FSH injections (twice daily for 4 days) 8 days after oestrus
(c) Give Estrumate again on morning of the third day of O-FSH treatment
(d) Examine ovulations by laproscope 7 days after oestrus or fertilized embryos by non-surgical flushing.

Trial 8

Field trials conducted on pre-pubescent female cattle of 10 months of age on the Potency of Ovine FSH

TABLE 9

|  | Dose mg Total | Cattle Treated | Ovulated Following treatment | Ovulation Rate Mean | Range |
|---|---|---|---|---|---|
|  |  | Hereford Cattle |  |  |  |
| O-FSH | 8 mg | 8 | 8 | 6.9 | 1-14 |
|  |  | Dexter Cattle |  |  |  |
| O-FSH | 20 mg | 2 | 2 | 14.6 | 13-16 |

Observations on Trial 8

Similar results with young cattle have not been achieved by other researchers using P-FSH.

EXAMPLE 6

Induction of Twinning in cattle using O-FSH

A field trial was conducted on 3 year old female Hereford cattle to illustrate the method of inducing twinning in female cattle according to the present invention.

Treatment Protocol

Same as for Example 5.

| 8 mg as follows: | Day 1 - am | 1.6 |
|---|---|---|
|  | - pm | 1.6 |
|  | Day 2 - am | 1.2 |
|  | - pm | 1.2 |
|  | Day 3 - am | 0.8 |
|  | - pm | 0.8 |
|  | Day 4 - am | 0.4 |
|  | - pm | 0.4 |

Trial 9

3 year old Cattle Born 1983

TABLE 10

|  | Dose Total mg | Cattle Treated | Ovulated Following treatment | Ovulation Rate Mean | Range |
|---|---|---|---|---|---|
| O-FSH | 8 | 19 | 19 | 2.4 | 1-9* |

*Only 3 cattle had ≧ 4 ovulations.

Observations on Trial 9

Similar results using P-FSH have not been obtained by other researchers.

"Simplification of O-FSH treatment" for the induction of Twinning in Cattle

Three regimens for FSH treatment to induce a mild increase in ovulation rate were trialed. Compared were the standard regime (8 injections over 4 days, beginning 48 hours before injection of Estrumate), and two 24 hour treatments beginning before or at the time of the injection of Estrumate. The cattle used were of mixed genotype and were aged from 2-3 years.

Injection Protocol for O-FSH

Commence FSH treatment at day 10 of oestrous cycle.
A. Standard protocol—as described in Example 6.
B. At 0900, 1500 2100 day 11 of cycle and 0300 day 12 of cycle.
C. At 0900, 1500, 2100 day 12 of cycle and 0300 day 13 of cycle.

Estrumate injected at 0900 on day 12 of cycle for treatment groups A, B and C.

For treatment B and C O-FSH injected as 4 equal amounts of 2 mg.

Treatment Protocol

As for Example 5.

Trial 10

O-FSH Injection Protocols for the induction of Twinning in cattle

TABLE 11

|  | Cows 2-3 Years of Age | | | | | |
|---|---|---|---|---|---|---|
| Treatment | No. Cows | No. Cows with zero ovulations | No. Cows. with 1 ovulation | No. Cows with ≧ 1 ovulations | Mean Ovulations | Range |
| Nil (Saline) | 9 | 2 | 7 | 0 | 1.0 | 1-1 |
| A. 8 mg O-FSH over 4 days | 9 | 0 | 4 | 5 | 3.3 | 2-11 |

TABLE 11-continued

| Treatment | Cows 2-3 Years of Age | | | | | |
|---|---|---|---|---|---|---|
| | No. Cows | No. Cows with zero ovulations | No. Cows. with 1 ovulation | No. Cows with ≧ 1 ovulations | Mean Ovulations | Range |
| B. 8 mg O-FSH over 24 hrs | 9 | 0 | 3 | 6 | 2.9 | 2-7 |
| C. 8 mg O-FSH over 24 hrs | 9 | 0 | 4 | 5 | 3.0 | 2-9 |

Observations on Trial 10

1. All 3 O-FSH treatments produced comparable results.
2. The standard regime, 8 injections over 4 days is more complex than necessary for the induction of 2-3 ovulations.

EXAMPLE 7

Effect of body weight and age on the induction of twinning in cattle by the use of O-FSH A number of field trials were undertaken to assess the importance of body weight and the age of cattle on the induction of twinning using the standard dose of 8 mg and the standard protocol of 8 injections over 4 days.

Trial 11

Effect of Age on the induction of twinning with 8 mo O-FSH

Hereford Cattle: 8 mo O-FSH

TABLE 12

| TREATMENT | No. Treated | Ovulated Following Treatment | Ovulation Rate | |
|---|---|---|---|---|
| | | | Mean | Range |
| Age 2 Years | 8 | 8 | 6.9 | 1-14 |
| 3 Years | 19 | 19 | 2.42 | 1-9 |

Trial 12

Effect of Age and Bodyweight on the induction of twinning with 8 mg O-FSH

Hereford Cattle: 8 mg O-FSH

TABLE 13

| TREATMENT | Live Body Weight (kg) Mean | No. Treated | Mean Ovulation Rate |
|---|---|---|---|
| Age 4 Years | 451 | 12 | 2.9* |
| 3 Years | 420 | 8 | 3.4* |
| 2 Years | 260 | 8 | 9.5* |

*90% of the cattle in these treatment groups were diagnosed as pregnant

* 90% of the cattle in these treatment groups were diagnosed as pregnant

Observations on Trials 11 and 12

Need to carefully calculate amount of O-FSH to achieve twinning with regard to age and body weight.

Finally, it is to be understood that various other modifications and/or alterations may be made without departing from the spirit of the present invention as outlined herein.

I claim:

1. A method of increasing the number of ova produced during ovulation in a female animal, comprising a step of administering to the animal an ovine follicle-stimulating hormone isolated from ovine pituitary glands in an amount of about 4-30 mg for a time sufficient to induce increased ova production.

2. A method according to claim 1 wherein said step of administering the ovine follicle-stimulating hormone comprises administering about 3-10 mg of the ovine follicle-stimulating hormone per day, reducing to about 0.4-2 mg of the ovine follicle-stimulating hormone per day, over a period of 3 to 4 days.

3. A method according to claim 2 further including a preliminary step of administering to the animal an effective amount of a synchronizing agent about 8 to 15 days prior to initiation of said administering of said ovine follicle-stimulating hormone.

4. A method according to claim 3 wherein about 250 ug to about 100 mg of the synchronizing agent is administered to the animal.

5. A method according to claim 1 further comprising a step of administering to the animal an effective amount of a luteinizing agent before, during or after said step of administering the ovine follicle-stimulating hormone.

6. A method according to claim 5 wherein the luteinizing agent is a prostaglandin or a prostaglandin analogue, and the luteinizing agent is administered in an amount of about 250 ug to about 1000 ug approximately 1 to 3 days after the initiation of said administering of the ovine follicle-stimulating hormone.

7. A method according to claim 1 further comprising a step of administering to the animal an effective amount of a gonadotrophin before or during said step of administering the ovine follicle-stimulating hormone.

8. A method according to claim 7 wherein the gonadotrophin comprises pregnant mare serum gonadotrophin, and wherein about 100-1000 i.u. of the gonadotrophin is administered to the animal during a first day of said administering of the ovine follicle-stimulating hormone.

9. A method of increasing ovulation to produce twinning in female cattle, comprising a step of administering to a female cow an amount of about 1-20 mg of an ovine follicle-stimulating hormone isolated from ovine pituitary glands.

10. A method according to claim 9 further comprising a preliminary step of administering to the cow an effective amount of a synchronizing agent approximately 8 to 15 days prior to initiation of said step of administering the ovine follicle-stimulating hormone.

11. A method according to claim 9 further comprising a step of administering to the animal an effective amount of a luteinizing agent before, during or after said step of administering the ovine follicle-stimulating hormone.

12. A method according to claim 9 wherein said step of administering the ovine follicle-stimulating hormone comprises administering about 0.8-4 mg per day of the ovine follicle-stimulating hormone, reducing to about 0.2-1 mg per day of the ovine follicle-stimulating hormone, over a period of 3 to 4 days.

13. A method according to claim 9 wherein said step of administering the ovine follicle-stimulating hormone comprises administering about 1-10 mg of the ovine follicle stimulating hormone per day, in 1 to 5 doses, over a period of one day.

14. A method according to claim 13 further comprising a step of administering to the animal an effective amount of a luteinizing agent before, during or after said step of administering the ovine follicle-stimulating hormone.

15. A method of inducing ovulation in a pre-pubescent female animal, comprising a step of administering to the pre-pubescent animal about 1-20 mg per day of an ovine follicle-stimulating hormone isolated from ovine pituitary glands, for a period sufficient to induce ovulation.

16. A method according to claim 15 wherein said step of administering the ovine follicle-stimulating hormone includes administering about 2-4 mg per day of the ovine follicle-stimulating hormone, reducing to about 0.5-1 mg per day of the ovine follicle-stimulating hormone, over a period of about 3 to 5 days.

17. A method according to claim 16, further including a preliminary step of administering to the animal an effective amount of a synchronizing agent approximately 8 to 15 days prior to initiation of said step of administering the ovine follicle-stimulating hormone.

18. A method according to claim 17 wherein about 250 ug to about 100 mg of the synchronizing agent are administered to the animal.

19. A method according to claim 15, further comprising a step of administering to the pre-pubescent animal an effective amount of a luteinizing agent before, during or after said step of administering the ovine follicle-stimulating hormone.

20. A method according to claim 19 wherein the luteinizing agent comprises a prostaglandin or prostaglandin analogue, and about 250-1000 ug of the luteinizing agent is administered to the animal about 1 to 3 days after initiation of said step of administering the ovine follicle-stimulating hormone.

* * * * *